US010300224B2

(12) United States Patent
Morrison (10) Patent No.: US 10,300,224 B2
(45) Date of Patent: *May 28, 2019

(54) MEDICAL DEVICE NOTIFICATION SYSTEM

(71) Applicant: MicroDose Therapeutx, Inc., Ewing, NJ (US)

(72) Inventor: Mark Steven Morrison, Basking Ridge, NJ (US)

(73) Assignee: MicroDose Therapeutx, Inc., Ewing, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/937,015

(22) Filed: Mar. 27, 2018

(65) Prior Publication Data

US 2018/0207373 A1 Jul. 26, 2018

Related U.S. Application Data

(63) Continuation of application No. 15/173,084, filed on Jun. 3, 2016, now Pat. No. 9,937,305.

(Continued)

(51) Int. Cl.
*G08B 5/36* (2006.01)
*A61M 15/00* (2006.01)
(Continued)

(52) U.S. Cl.
CPC ......... *A61M 15/0001* (2014.02); *G06F 19/00* (2013.01); *G06F 19/3418* (2013.01);
(Continued)

(58) Field of Classification Search
None
See application file for complete search history.

(56) References Cited

U.S. PATENT DOCUMENTS 7,318,434 B2   1/2008   Gumaste et al.
7,715,277 B2   5/2010   De La Huerga
(Continued)

FOREIGN PATENT DOCUMENTS

WO   WO 2001/097889 A2   12/2001
WO   WO 2002/000281 A2    1/2002
(Continued)

OTHER PUBLICATIONS

Wikipedia, "Bluetooth", Available at https://en.wikipedia.org/wiki/Bluetooth, Mar. 3, 2013, 21 pages.
(Continued)

*Primary Examiner* — Brian A Zimmerman
*Assistant Examiner* — Renee Dorsey
(74) *Attorney, Agent, or Firm* — Condo Roccia Koptiw LLP (57) ABSTRACT

A system and method for communicating data from a medical device to a lighting device is provided. The system may include the medical device, the lighting device, and/or one or more interface devices. The medical device may be configured to transmit data to the lighting device, which for example, may include information relating to the medical device, dosage information, diagnostic data, medical device training feedback, health monitoring information, and/or air quality information. The lighting device may be configured to receive data from the medical device and control one or more lighting characteristics based on the received data. A characteristic of the light may include one or more of color, color temperature, intensity, flashing or steady-state, on or off, and/or the like. The system may provide for a home based adherence and/or compliance monitoring system, in which a patient's interaction with a medical device may be monitored and an alert/indication provided.

20 Claims, 2 Drawing Sheets

Related U.S. Application Data (60) Provisional application No. 62/170,350, filed on Jun. 3, 2015.

(51) Int. Cl.
  G06F 19/00 (2018.01)
  G16H 20/10 (2018.01)
  G16H 40/63 (2018.01)

(52) U.S. Cl.
  CPC .............. *G08B 5/36* (2013.01); *G16H 40/63* (2018.01); *A61M 2205/18* (2013.01); *A61M 2205/583* (2013.01); *A61M 2230/42* (2013.01); *G06F 19/3456* (2013.01); *G16H 20/10* (2018.01)

(56) References Cited

U.S. PATENT DOCUMENTS

| | | | |
|---|---|---|---|
| 8,439,033 B2 | 5/2013 | Gumaste et al. | |
| 8,725,291 B2 | 5/2014 | Czaja et al. | |
| 9,474,695 B1* | 10/2016 | Khalid | A61J 7/0409 |
| 2007/0016443 A1 | 1/2007 | Wachman et al. | |
| 2011/0000481 A1 | 1/2011 | Gumaste et al. | |
| 2011/0162642 A1 | 7/2011 | Akouka et al. | |
| 2012/0038226 A1 | 2/2012 | Tran et al. | |
| 2012/0313785 A1* | 12/2012 | Hanson | G08B 21/24 340/573.1 |
| 2013/0002795 A1 | 1/2013 | Shavelsky et al. | |
| 2013/0030566 A1 | 1/2013 | Shavelsky et al. | |
| 2013/0197693 A1 | 8/2013 | Kamen et al. | |
| 2014/0116426 A1* | 5/2014 | Mullinger | A61M 11/005 128/200.14 |
| 2014/0137737 A1* | 5/2014 | Wilkinson | A61M 16/10 95/130 |
| 2014/0137744 A1* | 5/2014 | Wilkinson | B01D 53/047 96/152 |
| 2014/0188348 A1 | 7/2014 | Gautama et al. | |
| 2014/0251330 A1* | 9/2014 | Collins | A61M 15/0086 128/203.14 |
| 2014/0352690 A1* | 12/2014 | Kolb | A61M 15/0085 128/200.14 |
| 2015/0068528 A1* | 3/2015 | Ahmad | A61M 16/026 128/204.23 |
| 2015/0077737 A1 | 3/2015 | Belinsky et al. | |
| 2015/0137994 A1* | 5/2015 | Rahman | H04Q 9/04 340/870.07 |
| 2015/0283036 A1 | 10/2015 | Aggarwal et al. | |
| 2016/0012702 A1* | 1/2016 | Hart | G08B 21/043 340/584 |
| 2016/0213865 A1* | 7/2016 | Poree | A61M 15/00 |

FOREIGN PATENT DOCUMENTS

| | | |
|---|---|---|
| WO | WO 2005/034833 A2 | 4/2005 |
| WO | WO 2014/106056 A2 | 7/2014 |

OTHER PUBLICATIONS

Wikipedia, "Wireless Repeater", Available at https://en.wikipedia.org/wiki/Wireless_repeater, Jan. 8, 2015, 2 pages.

* cited by examiner

MEDICAL DEVICE NOTIFICATION SYSTEM

CROSS-REFERENCE TO RELATED APPLICATIONS

This application is a continuation of U.S. patent application Ser. No. 15/173,084, filed Jun. 3, 2016, which claims the benefit of U.S. Provisional Patent Application No. 62/170,350, filed Jun. 3, 2015, the contents of which are incorporated by reference herein.

BACKGROUND

A patient's adherence relates to a patient taking their medication at the prescribed frequency, and is important to obtain the full benefits of the therapy. Similarly, it is also important that a patient are using their medication delivery device correctly. This is referred to as competence or compliance. It is valuable to monitor patient competence/compliance since a patient may be fully adherent to their medication schedule, but if they fail to use the device correctly, then they may receive an ineffective amount of the drug and therefore their therapy may be unsuccessful.

Providing a medical device with electronics configured to monitor patient usage is one method to allow for a patient or caregiver to ensure that medications are being taken correctly. It is known for drug delivery devices, such as inhalers and pill bottles, to use electronics that fit inside or attach to the body of medical devices and that these drug delivery devices may be configured to provide information regarding a patient's use of the device. These systems may provide reminders to patients in the form of visible or audible alerts, for example, when a dose is overdue or a medication has been administered correctly.

A problem experienced by such devices is that the additional electronics required significantly increase the manufacturing costs that most pharmaceutical companies are not willing to accept. Furthermore, such systems often require a certain level of engagement by the patients themselves, which may represent a further burden in addition to taking the medications themselves. As such, many patients are not willing to embrace the new technology and may be deterred from their continued adherence with their prescribed therapy. Accordingly, there exists a need for providing a convenient and inexpensive technique for improving the interaction of a user with a medical device that may not require much active participation on the part of the patient, may further engage the patient in their therapy, and/or may assist with competence/compliance monitoring.

SUMMARY

The present disclosure relates generally to communications between a medical device and one or more lighting devices. For example, embodiments described herein may provide a method of transmitting data from a medical device to a lighting device and modifying one or more characteristics of light emitted by the lighting device based on the data received. Advantageously, this system may be used to implement a home based adherence and competence/compliance monitoring system, in which a patient's interaction with a medical device may be monitored and a corresponding indicator may be provided to the patient or care provider through a change in a lighting characteristic of the lighting device (e.g., color, color temperature, intensity, flashing, on/off, etc.).

A method of communicating data from a medical device to a lighting device may be provided. Data may be transmitted from the medical device to the lighting device. The lighting device may be remote from the medical device. The lighting device may receive the data, directly or indirectly (e.g., via an interface device, such as a wearable or central hub), and the lighting device may be controlled in response to the data received from the medical device (e.g., a characteristic of the light may be adjusted accordingly). This change in the lighting device may provide feedback to a patient regarding the patient's interaction with a medical device. This may provide for a reduction in overall cost to the patient, for example, since feedback on multiple medical devices may be provided to a patient using one system rather than installing individually configured components in each medical device. Furthermore, such a system may be easier for a user to acclimate, for example, because it may use little or no user involvement to implement and/or maintain. Moreover, an easily recognizable signal to a patient, such as changing a characteristic of a light, is more likely to be viewed by a patient.

Using a lighting device, for example a smart light emitting diode (LED) light engine, the color, color temperature, intensity, and/or other characteristic of the light may be varied to provide one or more alerts/notifications to the patient. These alerts may provide a non-obtrusive method of providing information regarding device usage to the patient. The systems and/or methods described herein may be integrated with an existing home room-lighting device or system.

The data may be transmitted from the medical device to the lighting device using wireless communication (e.g., Bluetooth (e.g., BLE), Wi-Fi, ZigBee, etc.). The lighting device may be a smart LED device. The smart LED device may include one or more LEDs, and the illumination characteristics of the one or more LEDs may be based on data received from a medical device. The variable characteristic of the light may include one or more of: turning the light on/off (e.g., whether the light is emitting light or not emitting light); the color of the emitted light; the color temperature of the emitted light; the intensity of the emitted light; and/or flashing of the light on/off (e.g., to periodically emit light).

The lighting device (e.g., in a default state) may provide conventional room lighting. The lighting device may be configured to provide changes in a lighting characteristic based on receiving data transmitted from a medical device. The lighting device may be a dedicated lighting device for provided alerts/notifications to a user regarding a medical device (e.g., a dedicated plug-in lighting device). The lighting device may be a standalone, battery powered device.

The medical device may include medication. For example, the medical device may include an injectable medication device, a pill container, an inhaler, and/or the like. Data may be transferred from the medical device to the lighting device via one or more interface devices. For example, an interface device may include one or more of a smartphone, a smart television, an HDMI dongle, a wearable device (e.g., a smart watch), a tablet, a personal computer (PC), a wireless router, a bridge device configured to communicate by wireless communication with multiple lighting devices, etc. The medical device and lighting device may be in separate locations. The data may be transmitted (e.g., at least partially) via the internet. For example, if the interface device includes a wireless router, the wireless router may be connected to the Internet, and/or a smart phone or wearable may be connected to the Internet.

The data sent by the medical device may be based on internal operating conditions of the medical device. For example, the data may include information relating to one or more of the remaining battery life, the remaining number of doses, a device error, etc. The data sent by the medical device may be based on the interaction of a user with the medical device. For example, the data may include information relating to one or more of dose reminders, missed dose information, confirmation of proper device operation, patient coaching information, use errors, patient wellness information, etc. Data transmission from the medical device may be synchronized by a timer (e.g., included in the medical device). The data may be real-time data.

In one or more examples, the medical device may include an inhaler, the data may be sent by the medical device in real-time and may include patient inhalation data, and a characteristic of the lighting device may change based on a result of a comparison (e.g., a real-time comparison) between the patient inhalation data and target inhalation data stored in memory of the medical device. The target inhalation data may represent correct use of the medical device. For example, the data from the medical device may be stored in memory and analyzed over a period of time, and the data transmitted from the medical device to the lighting device may be dependent on the results of the analysis. The change in characteristic of the lighting device may include one or more of a change in color of the light and/or a change in intensity of the light.

The data may include environmental data, and the medical device (e.g., and/or any environmental monitor) may be configured to transmit the data to the lighting device upon a change in an environmental condition detected by the medical device. For example, the environmental condition may include at least one of temperature, humidity, pressure, acceleration of the medical device, carbon monoxide, etc.

A system may include a medical device and a lighting device. The medical device and lighting device may be configured to communicate with each other, for example, such that data from the medical device may be transmitted to the lighting device and a lighting characteristic of the lighting device may be controlled based on the received data. The system may include one or more interface devices. An interface device may be configured to communicate with at least one of the medical device, the lighting device, and/or another interface device. The medical device may be configured to transmit data to the lighting device via the one or more interface devices, and the lighting device may control at least one characteristic of the light based on the received data.

The system may be configured to determine (e.g., remotely determine) the interaction of a user with a medical device. The medical device may determine a user's interaction with the medical device using, for example, a motion detection device. The motion detection device may be remote from the medical device. The motion detection device may be coupled to the user through physical communication. The motion detector device may generate data based on a determined interaction between the user and the medical device. The motion detector may transmit (e.g., wirelessly transmit) the data to a remote device, which may be remote from the motion detection device. The motion detection device may, for example, include an accelerometer. The user's interaction with the medical device may be determined through physical communication between the user and the accelerometer of the motion detection device.

The remote device may include, for example, one or more of a smartphone, a smart television, an HDMI dongle, a lighting device, a wearable device, and/or a personal computer. The medical device may include one more of more an injectable medication device, a pill container, an inhaler, etc. The motion detection device may include a wearable device, which for example, may include a wristband device, a watch device, a ring device, a pendant device, and/or a smart textile device. The user's interaction with the medical device may be based on sensors of the medical device. The data from the sensors may be wirelessly transmitted between the medical device and at least one of the motion detection device and the remote device.

DETAILED DESCRIPTION

Figure 1:
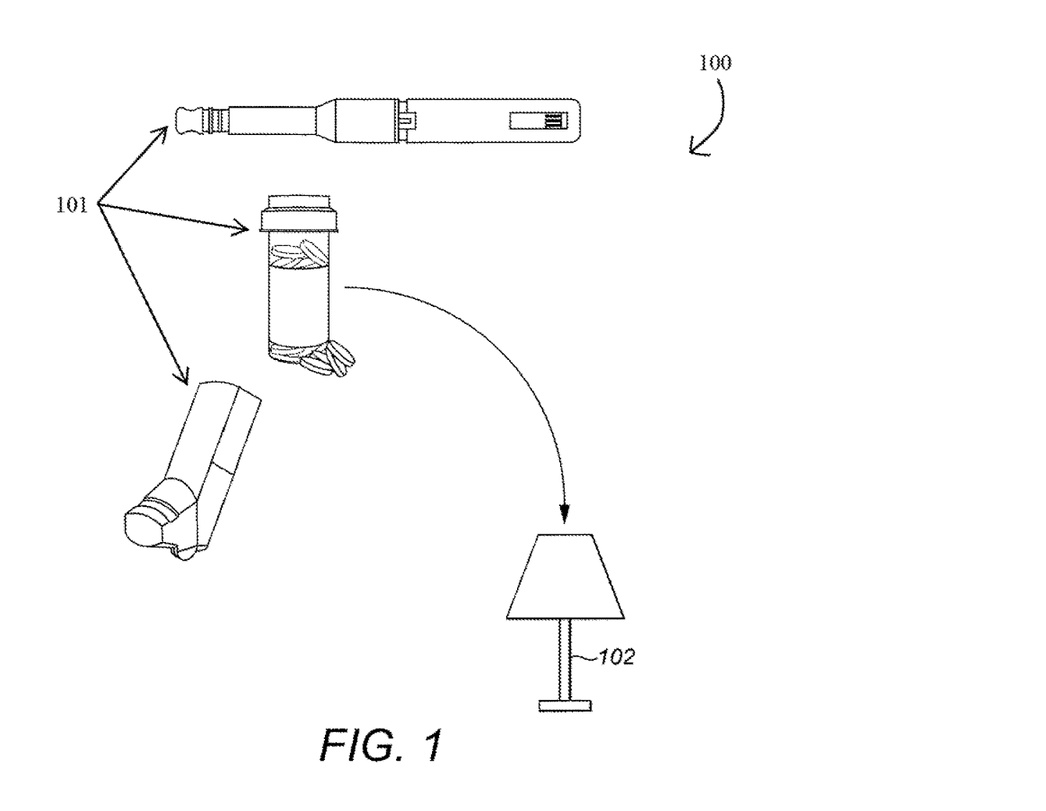
FIG. 1 is a diagram of an example of a medical device notification system.

FIG. 1 is a diagram of an example of a medical device notification system 100. The system 100 includes a medical device 101 and a lighting device 102. In one or more embodiments, the system 100 may include one or more interface devices (not shown). The system 100 is configured such that data may be sent from the medical device 101 to the lighting device 102, and one or more characteristics of light emitted by the lighting device 102 may be controlled based on the data received from the medical device 101.

The medical device 101 may be any type of medical device 101 capable of transmitting data. The medical device 101 may include medication. For example, the medical device 101 may be an inhaler, a pill container, or injectable medication device. The medical device 101 may include a processor, memory, a power storage device (e.g., a battery), and/or communication circuit. For example, the medical device 101 may be a small, handheld, battery operated, medical device. Alternatively, the medical device 101 may not include medication and, for example, may be used only for training and/or diagnostic purposes. The medical device may include one or more sensors. The sensors may include one or more of a flow sensor, a thermometer, an accelerometer, a pressure sensor, a humidity sensor, a carbon monoxide sensor, etc.

The processor may include a microprocessor, a programmable logic device (PLD), a microcontroller, an application specific integrated circuit (ASIC), and/or the like. The memory may be implemented as an external integrated circuit (IC) or as an internal circuit of the processor. The memory may operate to store information such as computer-executable instructions, configuration settings associated with operation of the medical device 100, and/or the like. The memory may include one or more components of volatile and/or non-volatile memory, in any combination.

The communication circuit may include a wireless transmitter and/or receiver (e.g., a wireless transceiver). The communication circuit may be configured to communication via one or more of Bluetooth (e.g., Low Energy Bluetooth (BLE)), Wi-Fi, ZigBee, Thread (e.g., Google Thread), and/or the like. Bluetooth may be used because it allows for low power data transmission, which for example, may be advantageous as it may be important to have low power demands on the battery of the medical device 101. Alternative or additionally, the communication circuit may include a wired data port and may be configured for a wired data communication, for example, to an interface device.

The medical device 101 may be configured to transmit data to the lighting device 102, either directly or indirectly (e.g., via one or more interface devices). The data provided by the medical device 101 may include information relating to the medical device 101, diagnostic data (e.g., a measurement from the one or more sensors of the medical device), medical device training feedback (e.g., coaching information and/or feedback), health monitoring information (e.g., lung function or other patient wellness information), air quality information/environmental information (e.g., temperature, humidity, barometric pressure, carbon monoxide), etc. The information relating to the medical device may include internal operating conditions of the medical device (e.g., remaining battery life, a device error, etc.), dosage information (e.g., a dose reminder, empty or low dose remaining information, remaining number of doses, missed dose information, etc.), confirmation of proper device operation, an indication of an incorrect use of the medical device (e.g., a use error), acceleration of the medical device (e.g., which may indicate that the device is being manipulated by the user (e.g., shaken, picked-up, etc.), the medical device was dropped, etc.), and/or the like.

The medical device 101 may be configured to receive a measurement from one or more sensors of the medical device 101. The data transmitted by the medical device may be the measurement information itself or data derived based on measurement information. For example, the medical device 101 may be configured to perform analysis of measurements before determining the data to transmit to the lighting device 102. The lighting device 102 and/or interface device may receive measurement information (e.g., data) from the medical device 101 and may perform the analysis itself. The analysis, for example, may be a comparison of the measurement to a threshold (e.g., predetermined threshold), a comparison of the measurement over time, etc. The transmitted data and/or measurements may be specific to the particular type of medical device and/or medicament.

The medical device 101 may, for example, include a tidal inhaler, such as a dry powder tidal inhaler. The dry powder tidal inhaler may include a piezo vibrator for aerosolizing the dry powder. The dry powder tidal inhaler may include dry powder medicament within blisters on a blister strip. Thy dry powder inhaler may be configured to advance the blister strip and open a blister such that the medicament may be transferred from the blister to a dosing chamber (e.g., via a short passageway). The dosing chamber may be in close proximity to or in contact with the piezo vibrator within the dry powder inhaler. The dosing chamber may include one or more apertures opposite the piezo to allow ejection of the powder into a passageway in contact with a mouthpiece or nosepiece for patient inhalation.

The medical device 101 may include a nebulizer, such as a dry powder nebulizer or a liquid nebulizer. The medical device 101 may include a flow sensor and/or a pressure sensor for monitoring a user's breathing, for example, such that corresponding data may be transmitted to the lighting device 102. Actuation of the piezo and thus ejection of the medicament from the dosing chamber for inhalation by the patient may be modulated by signals generated by the flow sensor and/or other patient activated controls.

The medical device 101 may, for example, include a dry powder inhaler. The dry powder inhaler may include a mouthpiece for patient inhalation, a delivery passageway for directing an inhalation induced air flow through the mouthpiece, a channel extending from the delivery passageway, and/or a reservoir for containing medicament. The reservoir may include a dispenser port connected to the channel. The dry powder inhaler may include a cover that, for example, may be pivotally mounted to the case of the inhaler for covering the mouthpiece and/or for actuating dispensing of medicament from the reservoir via a hopper. The inhaler may have a breath-actuated mechanism where inhalation by the patient induces delivery of the metered medicament.

The medical device 101 may, for example, be based on (e.g., include) one or more of the medical devices as disclosed in any of US 2011/0162642A1, U.S. Pat. No. 8,439,033B2, US 2011/0000481A1, U.S. Pat. No. 7,318, 434B2, WO 02/00281, WO 01/097889 and/or WO 2005/034833, with the medical device 101 further enabled for data communication, for example, as described herein. Thus, the medical device 101 may be based on a MicroDose® device or Spiromax®/DuoResp®Spiromax® device, manufactured by Teva®, with the medical device 101 further enabled for data communication, for example, as described herein. The medical device 101 may include a configurable platform device, for example, as described with reference to FIG. 3.

The lighting device 102 may be configured to receive data from the medical device 101. The lighting device 102 may be configured such that one or more lighting characteristics are controlled based on the data received from the medical device 101. A characteristic of the light may include one or more of color, color temperature, intensity, flashing or steady-state, on or off, and/or the like. For example, the lighting device 102 may adjust, based on data received from the medical device 101, whether individual lights (e.g., LEDs) are on and emitting light or off and not emitting light, the color of the emitted light, the color temperature of the emitted light, the intensity of the light emitted, flashing one or more lights, and/or any combination thereof. The lighting device 102 may be used to provide information regarding the medical device 101 and/or information relating to a patient's interaction with the medical device 101 to a patient and/or caregiver.

The lighting device 102 may be any suitable type of lighting device. The lighting device 102 may include a smart LED device, which for example, may include a transmitter and/or receiver (e.g., a transceiver), a processor (e.g., part of a controller), and one or more LEDs (e.g., LEDs and/or LED light engines). The processor of the lighting device 102 may be configured to receive messages from an external device (e.g., the medical device 101 and/or an interface device), interpreting the received messages, and control the output of light of the lighting device 102 accordingly. The lighting device 102 may be configured to control (e.g., adjust) one or more characteristics of the one or more LEDs based on data received from the medical device 101. The lighting device 102 may be configured to communicate with one or more interface devices, for example, to route data to and/or from the medical device 101, to provide advanced functionality, to provide user control of the lighting 102 device, and/or the like.

The system 100 may include one or more interface devices (not shown). The medical device 101 may be configured to transmit data to an interface device, which may route the data (e.g., directly or indirectly) to the lighting device 102. An interface device may include one or more of a smartphone, a smart television, a High-Definition Multi-media Interface (HDMI) connected device (e.g., dongle), a wearable device (e.g., a smart watch, a smart textile, etc.), a personal computer (PC), a tablet, a router (e.g., a wireless router), a bridge device configured to communicate by wireless communication with multiple lighting devices, a cloud server and/or cloud computing architecture, etc. The interface device may be configured to transmit data wirelessly and/or via a wired connection, and/or may be configured to receive data wirelessly and/or via a wired connection. For example, the medical device 102 may be configured to wirelessly transmit data to the interface device, which may be configured to wirelessly transmit the data to the lighting device 102. Alternatively, and for example, the medical device 101 may be configured to transmit data to the interface device via a physical, wired connection, and the interface device may wirelessly transmit the data to lighting device 102.

The lighting device 102 may, for example, include a Bluetooth LED Light Bulb, such as those offered by Roybens, MisFit (e.g. Bolt) and MiPow (e.g. Playbulb), which for example, may be controlled directly with a Bluetooth enabled device. The lighting device 102 (e.g., a Philips 'Hue' lighting system) may use a bridge device to control the lights, and/or a wireless router to interface with a smartphone and/or wearable. The Hue system may operate at higher power levels than a Bluetooth system and therefore may reach (e.g., directly reach) lighting devices located throughout a home. The bridge device may control one or more lighting devices 102 using timers to synchronize the lights to come on or turn off at pre-programmed times, and as such, may be configured provide various alerts to a patient (e.g., dose reminders). The lighting device 102 (e.g., and/or the bridge) may include a Bluetooth communication circuit (e.g., a mesh type BLE circuit) and may provide range extension for the lighting device 102 by communicating through other Bluetooth enabled devices, for example, without the need for a dedicated bridge, thus reducing cost.

The lighting device 102 may be powered by direct current (DC) or alternating current (AC). The lighting device 102 may include AC outlet prongs. The lighting device may comprise a battery and/or be battery powered (e.g., in addition to or alternative to having a plug for standard AC power). For example, a battery powered lighting device may be made of any appearance, such as a candle, nightlight, etc.

The lighting device 102 may be configured to provide ambient lighting. For example, the lighting device 102 may act as part of a home lighting system. As such, the lighting device 102 may provide both conventional room lighting and alerts based on data received from the medical device 101. For example, multiple lighting devices 102 may control one or more characteristics of their light based on data received from the medical device 101, for example, such that a user does not have to remember to check a dedicated lighting device and is more likely to receive the alerts provided. Alternatively, the lighting device 102 may be a dedicated light that provides alerts/notifications to a user of the medical device 101. For example, the lighting device 102 may be a plug-in device that is configured with alternating current (AC) outlet prongs, which may for example plug into a mains outlet (e.g., in a bathroom or bedroom). The latter option may be preferable if a patient does not want their regular room lighting to be disrupted.

The system 100 may use one or more one wired or wireless communication protocols when transferring data from the medical device 101 to the lighting device 102. For example, the medical device 101 may transmit data to an interface device using a first wireless communication protocol (e.g., Bluetooth), and the interface device may transmit data to the lighting devices 102 via a second wireless communication protocol (e.g., via Wi-Fi). The interface device (e.g., a bridge device) may provide increased communication range via wired communication (e.g., an Ethernet and/or Internet connection). The interface device may allow for control of a lighting device 102 that is out of range of wireless communication with the medical device 101 (e.g., such as a lighting device 102 in a remote caregiver's home).

The medical device 101 may be configured to transmit data directly to the lighting device 102. For example, the data transmitted by the medical device 101 to the lighting device 102 may be characterized by a defined lighting protocol, such as the BLE GATT protocol, for example. The lighting protocol may include a list of services and characteristics, such as lamp control, lamp color, etc. that are predefined for control of the lighting device 102.

The medical device 101 and/or an interface device may receive a broadcast message (e.g., an advertisement) from the lighting device 102. The broadcast message may indicate that the lighting device 102 is available for communication. The medical device 102 or the interface device may connect to the lighting device 102, for example, after receiving the broadcast message. The lighting device 102 may be unavailable to connect with other devices after connecting to the medical device 102 or the interface device. The connected device (e.g., the medical device 101 and/or the interface device) may transmit data (e.g., issue one or more commands) to the lighting device 102 to control the light output of the lighting device 102.

Figure 2:
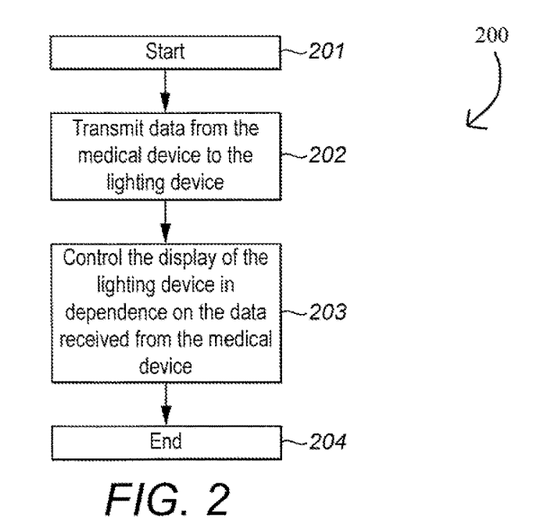
FIG. 2 is a flowchart of an example notification procedure that may be performed by a medical device notification system.

FIG. 2 is a flowchart of an example procedure 200. The procedure 200 may be performed by a medical device notification system, for example, the system 100 or the system 300. At 201, the procedure begins. In step 202, a medical device transmits data to a lighting device. For example, the data may include information relating to the medical device 101, diagnostic data, medical device training feedback (e.g., coaching information and/or feedback), health monitoring information (e.g., lung function or other patient wellness information), air quality information/environmental information (e.g., temperature, humidity, barometric pressure, carbon monoxide), etc. The information relating to the medical device may include internal operating conditions of the medical device (e.g., remaining battery life, a device error, etc.), dosage information (e.g., a dose reminder, empty or low dose remaining information, remaining number of doses, missed dose information, etc.), confirmation of proper device operation, an indication of an incorrect use of the medical device (e.g., a use error), acceleration of the medical device (e.g., which may indicate that the device is being manipulated by the user (e.g., shaken, picked-up, etc.), the medical device was dropped, etc.), and/or the like.

At step 203, the lighting device may control one or more characteristics of light based on the data received from the medical device, for example, such that information relating to the medical device may be communicated to a patient and/or caregiver. For example, the lighting device may be configured to control whether individual lights (e.g., LEDs) are on and emitting light or off and not emitting light, the color of the emitted light, the color temperature of the emitted light, the intensity of the light emitted, flashing one or more lights, and/or any combination thereof. At step 204, the procedure 200 ends.

Figure 3:
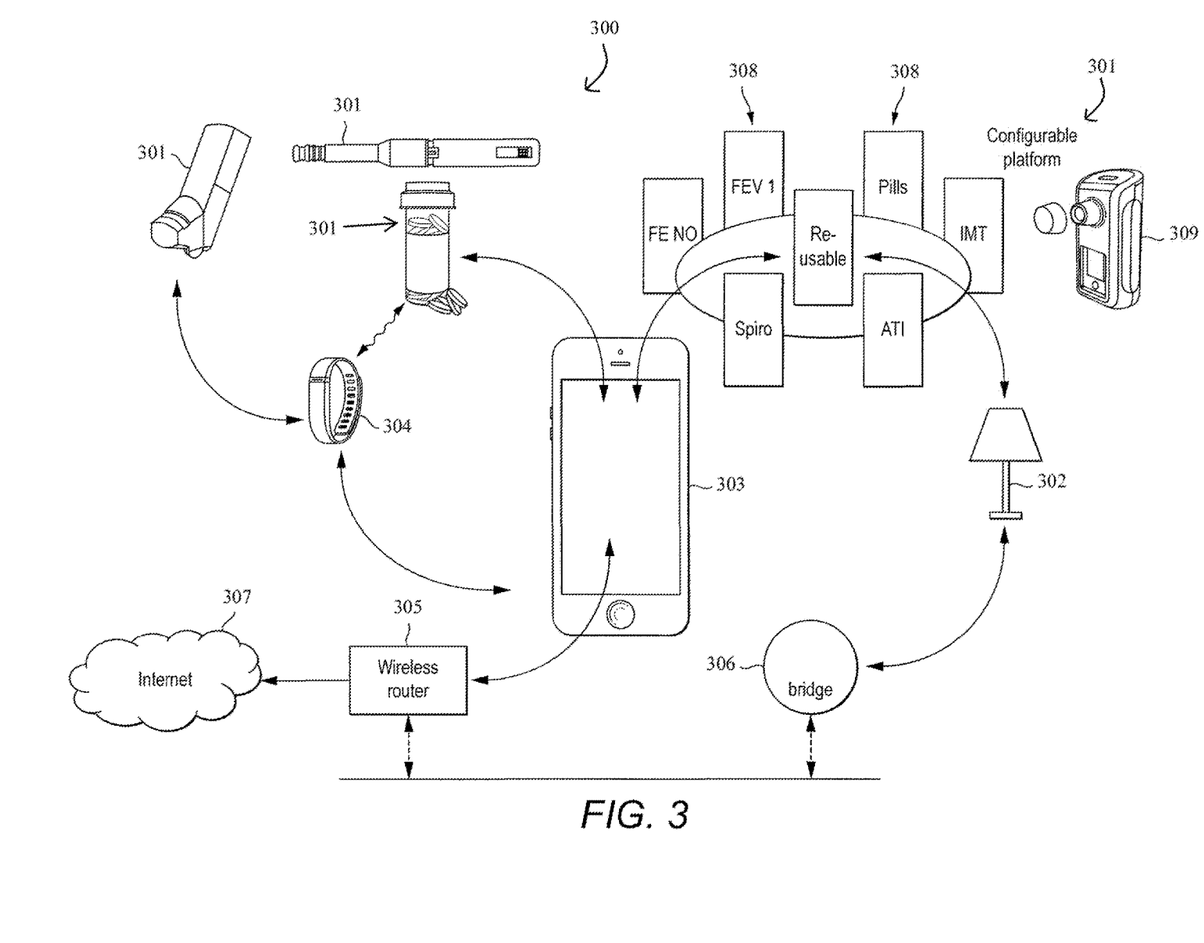
FIG. 3 is a diagram of another example of a medical device notification system.

FIG. 3 is a diagram of an example system 300. The system 300 may be an example of the system 100. The system 300 may include a medical device 301, a lighting device 302, and one or more interface devices. The medical device 101 may be an example of the medical device 301. For example, the medical device 301 may include an inhaler, a pill container, injectable medication device, and/or a configurable platform device. The lighting device 102 may be an example of the lighting device 302. For example, the lighting device 302 may include a smart lighting device. The interface devices may include any of the interfaces devices described with reference to FIG. 1. For example, an interface device may include a smartphone 303, a wearable device 304, a wireless router 305 (e.g., which may be connected to the internet 307), a bridge device 306, and/or a wireless wall outlet device (not shown). The bridge device may control a plurality of lighting devices 302 across a home.

The medical device 301 may include a configurable platform device. A configurable platform device may include a common user interface 309 that may be configured for exchangeable attachment to multiple, different modules 308, where each module may provide a different function. For example, the configurable platform device may include separate modules 308 for drug delivery (e.g., pills, dry powder, etc.), measuring lung function (e.g., FEV1), detecting certain markers in a user's breath (e.g., FE NO), coaching (e.g., IMT), measuring environmental factors, and/or the like. In such instances, the medical device 301 may collect information via various modules and communicate the information to one or more lighting devices 302 by means of a single common user interface platform.

In the system 300, the medical device 301 may be configured to transmit data, via one or more of the interface devices, to a lighting device 302. An interface device may have a larger memory than that of the medical device 301. Data generated by the medical device 301 may be transmitted (e.g., automatically transmitted) to an interface device for storage. Calculations and/or analysis on the data may be performed by a processor of the interface device, which for example, may have higher capabilities than the processor of the medical device 301. The interface device may transmit data relating to results of the analysis to the lighting device 302, which may change a characteristic of light accordingly.

The smart phone 303 may allow for implementation of intelligent control for more advanced functions in the system 300. The smartphone 303 may provide a user-friendly interface for a patient to program the system 300 to set their preferences for the alerts provided by the lighting device 302 and/or the lighting characteristics that are changed for each type of alert. The interface device may include a smart television, or a conventional television using an HDMI dongle, TV stick, TV box, and/or conventional set top box, that may provide a user interface to allow interaction and/or customization of the system 300. The lighting device 302 may provide a notification that prompts the patient to read a message delivered to the interface device (e.g., smartphone, smart television, HDMI dongle, etc.).

The interface device (e.g., a wearable devices 304) may include a processor, memory, LEDs, an accelerometer, a vibrator, one or more sensors, and/or a wireless communication circuit (e.g., Bluetooth). The wireless communication circuit may be used to interface to another interface device (e.g., the smartphone 303). Utilizing such an interface device may allow for the system 300 to be realized even if the medical device 301 itself is not fitted with the necessary electronics to transmit data to the lighting device 302. For example, if the wearable device 304 is worn on the patient's wrist, the accelerometer of the wearable device 304 may detect shaking of a pill container, dispensing of a pill from the container, and/or any other user gesture characteristic of usage of the medical device 301. In this way, the wearable device 304 may, for example, sense when a medication has not been taken, since the required user gesture has not been sensed by the accelerometer in a predefined time period, and data may be transmitted to the lighting device 302 to provide a late dose reminder. In such an embodiment, step 202 may be provided via two sub-steps with data first transmitted from the medical device 301 to the wearable device 304, and secondly with data (e.g., the same or different data) then transmitted from the wearable device 304 to the lighting device 302, for example, possibly via other interface devices such as the smart phone 303 and/or wireless router 305.

The system 300 may use the wearable device 304 to notify a patient as to whether or not they have taken their medication, for example, if they cannot remember taking it. For example, the patient may shake the medical device 301 (e.g., the pill container), which may be sensed by the accelerometer of the wearable device 304. The detection of this gesture causes the wearable device 304 to determine (e.g., by looking up in memory) whether a pill has been taken that day or not. The wearable device 304 may transmit a corresponding data signal to the lighting device 302 accordingly, and the lighting device 302 may change a characteristic of light (e.g., color) to notify the patient of the answer (e.g., green for yes and red for no). Further, the wearable device 304 may notify the user, for example, by vibrating to provide the user with an indication (e.g., a confirmation of proper use, etc.)

The use of one or more interface devices may allow for the medical device 301 to include less electronics, which for example, may further reduce costs of implementing the system 300. The medical device 301 may include (e.g., only include) simple electronic components to provide a wireless signal (e.g., a Bluetooth signal, an RFID tag, etc.) such that an interface device (e.g., the wearable device 304 and/or smartphone 303) may detect when the medical device 301 is within a certain proximity and register the event as a user interaction with the medical device 301. As such, the system 300 may provide substantial cost savings due to the reduction in complex electronics within the medical device 301, but also provide a more reliable method of sensing when the medical device 301 is being used compared to solely relying on the interface device (e.g., the accelerometer of the wearable device 304).

The system 300 may include the wireless router 305 connected to the Internet 307, and/or the interface device (e.g., a wearable 304 or smartphone 303) medical device 301 may access the Internet 307 directly. The system 300 may provide for updates to the software installed on one or more of the devices (e.g., the medical device 301, the lighting device 3020, and/or an interface device), for example, via the Internet 307. The system 300 may allow the data transmitted by the medical device 301 and/or interface device to be sent to a remote location. For example, the medical device 301 may transmit the data to a lighting device 302 in a caregiver's home or place of work. For example, if the medical device 301 senses that a patient has missed several doses of medication, the medical device 301 may transmit data across the Internet 307 to a lighting device 302 in the caregiver's home to notify them of a possible medical emergency.

The system 300 may include (e.g., or interface with) a home security system. For example, an accelerometer within a medical device 101 may be used as a fall detection system and alert the security monitoring system of such an event. The system 300 may change a characteristic of light (e.g., flash lights on and off) to alert others. The system 300 may transmit the data to a care provider and/or hospital. The system 300 may extend the monitoring of home security systems beyond fire and security applications to provide home healthcare monitoring. The system 300 may also communicate with the user's cable or satellite box.

Embodiments of the present invention may provide a convenient and inexpensive technique for improving the interaction of a user with their therapy via the provision of a user-friendly adherence and compliance home monitoring system. The use of a single system, provided by a home lighting system, in order to notify patients and caregivers of medical information may reduce the costs associated with introducing additional hardware to individual medical devices. The lighting device 302 may provide an unobtrusive yet easily recognizable signal to a patient. The lighting device 302 may require little or no active patient participation, and therefore overcome the problems of the known systems associated with a reliance on user interaction, which may deter patients from maintaining their therapy.

Several illustrative examples of compliance and adherence systems will now be described, which may be performed by the system 100 of FIG. 1 and/or the system 300 of FIG. 3. It will be understood that these examples are non-exhaustive and many more examples, utilizing differing medical devices, patient interaction parameters, and changes in lighting characteristics (e.g., lighting display changes) may be readily achieved with the system 100 of FIG. 1 and/or the system 300 of FIG. 3.

In one or more embodiments, the medical device may include an inhaler and the lighting device may include a smart LED device that forms part of a patient's home lighting system. The medical device may transmit data (e.g., directly or indirectly) to the lighting device if no user interaction is sensed by a flow sensor within the medical device within a certain time period of a predetermined medication time (e.g., which may be determined based on a dosage regimen). The synchronization of this initial data may be achieved by timers within the medical device itself, within the lighting device, and/or within an interface device. Upon receipt of the data, the lighting device may change, for example, its display color to notify the patient that they missed a scheduled dosage regimen. This change in color of one or more lights in the patient's home would then alert the patient to take their medication. Upon using the medical device, the flow sensor may sense the medication has been administered correctly and the medical device may transmit second data to the lighting device, accordingly. When the lighting device receives the second data, the lighting device may return to the original color (e.g., including white) or turn off if previously off before the first data was transmitted.

A system may also provide compliance monitoring and/or coaching to a patient. For example, the medical device may include an inhaler and the lighting device may include a smart LED device that forms part of a patient's home lighting system. The medical device may include one or more sensors that may measure one or more inhalation metrics of the patient. For example, when using the medical device, the flow sensor may detect the air flow rate related to the patient's inhalation and compare the air flow rate against data relating to an optimal inhalation flow rate, stored in memory in the medical device. The medical device may determine whether the measure flow rate is within one or more predefined thresholds and transmit data to the lighting device accordingly. The lighting device may receive the data from the medical device and alter a characteristic of light accordingly. For example, the lighting device may display a first color of light (e.g., green) if the inhalation flow is within an acceptable value range of the optimum value, a second color of light (e.g., red) if greater than the target flow rate window, and a third color of light (e.g., blue) if below the target flow rate window. In this way, real time feedback or coaching may be provided to the patient during use of the medical device. Alternatively or additionally, the medical device may determine the flow rate of the user and control the intensity of light of the lighting device according to the flow rate, for example, such that higher flows results in higher intensity light and lower flows result in lower intensity light. In one or more embodiments, the medical device may transmit the data to an interface device (e.g., the data may be raw measurement data), which may determine whether the measurement is within a predefined threshold and signal the lighting device accordingly. If, for example, the medical device is providing medication to the user, then the procedure may be considered compliance monitoring and/or provide real-time coaching. Alternatively, if no medication is being provided to the user, the procedure may be considered a training technique for the patient.

The medical device may measure an inhalation of a user and transmit first data to the lighting device, such that the lighting device controls a characteristic of the light (e.g., setting to a first color, flashing the light, turning on, etc.), which for example, may indicate to the user that they are inhaling at the proper rate. If the inhalation metric stays above a threshold for an amount of time, the medical device may transmit second data to the lighting device, such that the lighting device controls a characteristic of the light (e.g., setting to a second color, turning off, stop blinking, etc.), which for example, may indicate to the user that they have completed proper inhalation. If the medical device determines that the flow rate has dropped below a threshold and/or the inhalation was not held for the predetermined amount of time, the medical device may transmit third data to the lighting device, such that the lighting device controls a characteristic of the light (e.g., setting to a third color, blinking, etc.), which for example, may indicate to the user that they failed to have completed proper inhalation (failed compliance). Therefore, the system may be used to help a patient maintain a certain flow rate long enough to achieve a 'slow and deep' inhalation (e.g., for compliance and/or training purposes), which for example, may result in deep lung penetration for certain inhalers. Accordingly, the patient may be coached to maintain their inhalation rate such that a characteristic of the light (e.g., green light) is held constant for a time period indicative of proper 'slow and deep' inhalation, and the benefits of "slow and deep" breathing may be realized.

The system may provide patient health monitoring. For example, the medical device may include an inhaler and the lighting device may include a smart LED device that forms part of a patient's home lighting system. The patient's lung function may be measured by their inhalation flow rate as sensed by the flow sensor and/or the pressure sensor of the medical device. This data may be stored in memory, provided either in the medical device or an interface device, thereby keeping a record over time of the patient's lung function. If periodic analysis of the data indicates that the patient's lung function is deteriorating (e.g., despite the use data also indicating that the patient is adherent and/or compliant with their therapy), data may be transmitted to the lighting device and the lighting device may adjust a characteristic of light accordingly (e.g., flashing amber light). In this way, an early warning sign of a decline in patient health may be signaled, prompting the patient to seek medical help. Such a system may pick up early signs of a deterioration in health which otherwise would go unnoticed.

The system may be configured such that the medical device transmits data to the lighting device regarding device function (e.g., and potentially independent from patient use), such as battery life, remaining doses, device faults, etc. The medical device may include one or more sensors. The addition of various sensors within the medical device may allow the medical device to measure certain environmental and/or device conditions, such as temperature, acceleration, barometric pressure, humidity, carbon monoxide, etc. In this way, the medical device may sense if it has been left outside (e.g., based on temperature being below a threshold), if it has been dropped (e.g., based on acceleration data), and/or if environmental factors are such that there is a risk of the medication degrading or increased risk of need for the medication (e.g., as in increased risk of a flare up or exacerbation), for example, based on environmental temperature, barometric pressure, and/or humidity. Accordingly, the medical device may transmit data to the lighting device initiating a change in a characteristic of light to alert the user to the situation.

The system may be configured such that the medical device and/or an interface device may be configured to receive a notification via the Internet, and provide data based on the notification to the lighting device to alert the user. For example, the medical device and/or interface device may receive a notification relating to weather related data (e.g., pollen data), an offering of a new medication, a recall of a medication, etc. The system may be used to alert the user to check another device, such as an internet website or application (e.g., a television based application), for more information. For example, the lighting device may provide a notification to the user to turn on their TV.

The system may determine a particular lighting device(s) to control based on the location of the user. For example, the system may determine the location of the user based on an interface device (e.g., a wearable, a smartphone, a tablet, etc.), the medical device itself, and/or another device, such as a motion detector. The system may determine the lighting device(s) to control based on the location of the user, such that the lighting device(s) in the proximity of the user are illuminated to alert the user. The system may also utilize a mesh network of lighting devices and/or interface devices to assist with determining the location of the user and/or the particular lighting device(s) to control. For example, the lighting devices may transmit data originating from the medical device and/or interface device between one another. The lighting devices may form a mesh network with one another such that, for example, a plurality of lighting devices in proximity of the user are all controlled similarly.

The system may be configured to determine the interaction of a user with a medical device. The system may determine a user's interaction with the medical device using, for example, a motion detection device and/or a sensor integrated into the medical device. The motion detector device may generate data based on a determined interaction between the user and the medical device. The motion detection device may be remote from the medical device. The motion detection device may be coupled to the user through physical communication. For example, the motion detection device may include a wearable device, which for example, may include a wristband device, a watch device, a ring device, a pendant device, a smart textile device, etc. The motion detection device may, for example, include an accelerometer. The accelerometer may be used to determine whether a user interacts (e.g., shakes) the medical device.

The motion detector may transmit (e.g., wirelessly transmit) the data to a device that is remote from the motion detection device (e.g., a remote device). The remote device may include, for example, one or more of a smartphone, a smart television, an HDMI dongle, a lighting device, a wearable device, a personal computer, etc. The system may determine (e.g., confirm) the user's interaction with the medical device using one or more sensors of the medical device. The data from the sensors may be wirelessly transmitted by the medical device to at least one of the motion detection device and the remote device. Ultimately, the system (e.g., the medical device, the motion detector, and/or the remote device) may send data indicative of the user's interaction with the medical device to a lighting device, which in turn, may control a characteristic of light accordingly.

The system may determine whether the user is correctly using the medical device (e.g., in real-time). For example, the medical device may include an inhaler, the data may be sent by the medical device in real-time and may include patient inhalation data, and a characteristic of the lighting device may change based on a result of a comparison (e.g., a real-time comparison) between the patient inhalation data and target inhalation data stored in memory of the medical device. The target inhalation data may represent correct use of the medical device. For example, the data from the medical device may be stored in memory and analyzed over a period of time, and the data transmitted from the medical device to the lighting device may be dependent on the results of the analysis. If the medical device determines that the patient inhalation data and the target inhalation data are within a threshold indicative of proper inhalation, then the medical device may transmit data to the lighting device, and the lighting device may change a lighting characteristic accordingly (e.g., change the light to green). If the medical device determines that the patient inhalation data and the target inhalation data are not within a threshold indicative of proper inhalation, then the medical device may transmit data to the lighting device, and the lighting device may change a lighting characteristic accordingly (e.g., change the light to red, flash the light, etc.). As such, the user may receive feedback, in real-time, as to whether or not they are properly using their medical device. Alternatively, an interface device and/or the lighting load may receive data from the medical device (e.g., patient inhalation data) and perform the comparison.

The system may provide confirmation to the user that they correctly used a medical device. For example, the medical device may include an inhaler and the medical device may control a characteristic of the lighting device based on whether the user correctly inhaled. The inhaler may include a piezo vibrator for aerosolizing dry powder medication, and the inhaler may control a characteristic of the lighting device based on whether the user correctly inhaled and the piezo vibrator aerosolized the dry powder medication. This may provide comfort to patients otherwise uncertain that they have in fact correctly received a dose of medication, for example, since the dry powder medication may have no taste.

The system may use the lighting device to confirm feedback provided elsewhere in the system. For example, the medical device may include one or more lights (e.g., LEDs) that are used to provide feedback to the user while they are using the medical device (e.g., device primed, successful/unsuccessful inhalation, confirmation to the user that they correctly used a medical device, successful/unsuccessful transmission of data, etc.). The lighting device may mimic the lights of the medical device to provide confirmation of the feedback to the user.

Other embodiments of the invention will be apparent to those skilled in the art from consideration of the specification and practice of the embodiments disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claims set forth here below not be construed as being order-specific unless such order specificity is expressly stated in the claim.

What is claimed is:

1. A system comprising:
    a lighting device comprising a processor and a receiver;
    an inhaler comprising a processor, a pressure sensor, and a communication circuit, the communication circuit being configured to wirelessly transmit data to the lighting device; and
    an interface device comprising a processor and a communication circuit;
    wherein the processor of the inhaler is configured to receive patient inhalation data from the pressure sensor, and send the patient inhalation data to the interface device; and
    wherein the processor of the interface device is configured to:
        compare the patient inhalation data to target inhalation data, wherein the target inhalation data is representative of a target use of the inhaler by a user; and
        send data configured to control a characteristic of light emitted by the lighting device based on the comparison of the patient inhalation data to the target inhalation data.

2. The system of claim 1, wherein the interface device comprises one or more of a smartphone, a smart television, a high-definition multimedia interface (HDMI) dongle, a wearable device, a wireless router, a set-top box, or a bridge device.

3. The system of claim 1, further comprising a plurality of lighting devices, wherein the processor of the interface device is configured to:
    determine one or more lighting devices of the plurality of lighting devices that are in proximity of a user of the inhaler based on a signal received from at least one of the inhaler or the interface device; and
    control a characteristic of light emitted by the one or more lighting devices based on the data received from the interface device.

4. The system of claim 1, wherein the processor of the interface device is further configured to:
    send, to the lighting device, first data configured to control the light to a first color in response to a determination that a result of the comparison is within a threshold indicative of the target use of the inhaler; and
    send, to the lighting device, second data configured to control the light to a second color or to flash the light in response to a determination that the result of the comparison is not within the threshold indicative of the target use of the inhaler.

5. The system of claim 1, wherein the characteristic of the light comprises a color of the light, the patient inhalation data comprises an inhalation flow rate of the user of the inhaler, and the target inhalation data comprises a flow rate threshold, and wherein the processor of the interface device is further configured to:
    send, to the lighting device, first data configured to control the light to a first color in response to a determination that the inhalation flow rate is equal or greater than the flow rate threshold; and
    send, to the lighting device, second data configured to control the light to a second color in response to a determination that the inhalation flow rate is less than the flow rate threshold.

6. The system of claim 1, wherein the characteristic of the light comprises a color of the light, the patient inhalation data comprises an inhalation flow rate of the user of the inhaler, and the target inhalation data comprises a flow rate window, and wherein the processor of the interface device is further configured to:
    send, to the lighting device, first data configured to control the light to a first color in response to a determination that the inhalation flow rate is within the flow rate window;
    send, to the lighting device, second data configured to control the light to a second color in response to a determination that the inhalation flow rate is greater than the flow rate window; and
    send, to the lighting device, third data configured to control the light to a third color in response to a determination that the inhalation flow rate is below the flow rate window.

7. The system of claim 1, wherein the characteristic of the light comprises an intensity of the light, and the patient inhalation data comprises an inhalation flow rate of the user of the inhaler, and wherein the processor of the interface device is further configured to:
    send, to the lighting device, first data configured to control the light to a first intensity of the light in response to a first inhalation flow rate of the user of the inhaler; and
    send, to the lighting device, second data configured to control the light to a second intensity of the light in response to a second inhalation flow rate of the user of the inhaler, wherein the first inhalation flow rate is greater than the second inhalation flow rate, and the first intensity of the light is greater than the second intensity of the light.

8. The system of claim 1, further comprising a memory; wherein the processor of the interface device is further configured to:
    store the patient inhalation data in the memory;
    analyze the patient inhalation data periodically to determine whether a lung function of the user of the inhaler has deteriorated over time; and
    send, to the lighting device, data configured to control the light to flash in response to a determination that the lung function of the user of the inhaler has deteriorated over time.

9. The system of claim 1, wherein the characteristic of the light is at least one of a color of the light, a color temperature of the light, an intensity of the light, whether the light is flashing or in a steady-state, or whether the light is on or off.

10. The system of claim 1, wherein the lighting device is used to provide ambient light.

11. An interface device for communicating with an inhaler and a lighting device, the interface device comprising:
    a communication circuit configured to wirelessly transmit data to the lighting device; and
    a processor configured to:
        receive patient inhalation data from the inhaler;
        compare the patient inhalation data to target inhalation data, wherein the target inhalation data is representative of a target use of the inhaler by a user;

send data configured to control a characteristic of light emitted by the lighting device based on the comparison of the patient inhalation data to the target inhalation data.

12. The interface device of claim 11, wherein the interface device comprises one or more of a smartphone, a smart television, a high-definition multimedia interface (HDMI) dongle, a wearable device, a wireless router, a set-top box, or a bridge device.

13. The interface device of claim 11, wherein the processor is further configured to:
send first data configured to control the light to a first color in response to a determination that a result of the comparison is within a threshold indicative of the target use of the inhaler; and
send second data configured to control the light to a second color or to flash the light in response to a determination that the result of the comparison is not within the threshold indicative of the target use of the inhaler.

14. The interface device of claim 11, wherein the characteristic of the light comprises a color of the light, the patient inhalation data comprises an inhalation flow rate of the user of the inhaler, and the target inhalation data comprises a flow rate threshold, and wherein the processor is further configured to:
send first data configured to control the light to a first color in response to a determination that the inhalation flow rate is equal or greater than the flow rate threshold; and
send second data configured to control the light to a second color in response to a determination that the inhalation flow rate is less than the flow rate threshold.

15. The interface device of claim 11, wherein the characteristic of the light comprises a color of the light, the patient inhalation data comprises an inhalation flow rate of the user of the inhaler, and the target inhalation data comprises a flow rate window, and wherein the processor is further configured to:
send first data configured to control the light to a first color in response to a determination that the inhalation flow rate is within the flow rate window;
send second data configured to control the light to a second color in response to a determination that the inhalation flow rate is greater than the flow rate window; and
send third data configured to control the light to a third color in response to a determination that the inhalation flow rate is below the flow rate window.

16. The interface device of claim 11, wherein the characteristic of the light comprises an intensity of the light, and the patient inhalation data comprises an inhalation flow rate of the user of the inhaler, and wherein the processor is further configured to:
send first data configured to control the light to a first intensity of the light in response to a first inhalation flow rate of the user of the inhaler; and
send second data configured to control the light to a second intensity of the light in response to a second inhalation flow rate of the user of the inhaler, wherein the first inhalation flow rate is greater than the second inhalation flow rate, and the first intensity of the light is greater than the second intensity of the light.

17. The interface device of claim 11, further comprising a memory;
wherein the processor is further configured to:
store the patient inhalation data in the memory;
analyze the patient inhalation data periodically to determine whether a lung function of the user of the inhaler has deteriorated over time; and
send data configured to control the light to flash in response to a determination that the lung function of the user of the inhaler has deteriorated over time.

18. The interface device of claim 11, wherein the characteristic of the light is at least one of a color of the light, a color temperature of the light, an intensity of the light, whether the light is flashing or in a steady-state, or whether the light is on or off.

19. A method performed by an interface device that comprises a processor and a communication circuit, the method comprising:
receiving, with the processor of the interface device, patient inhalation data derived via a pressure sensor of an inhaler;
comparing, by the processor of the interface device, the patient inhalation data to target inhalation data, wherein the target inhalation data is representative of a target use of the inhaler by a user; and
sending, via the communication circuit of the interface device to a receiver of a lighting device, data configured to control a characteristic of light emitted by the lighting device based on the comparison of the patient inhalation data to the target inhalation data.

20. The method of claim 19, further comprising:
determining one or more lighting devices that are in proximity of the user of the inhaler based on a signal received from at least one of the inhaler or the interface device; and
controlling the characteristic of light emitted by the one or more lighting devices based on the proximity of the user of the inhaler and based on the data configured to control the characteristic of emitted light.

* * * * *